United States Patent [19]

Holtkamp, Sr.

[11] Patent Number: Plant 7,094

[45] Date of Patent: Jan. 2, 1990

[54] AFRICAN VIOLET PLANT LUCY

[76] Inventor: Reinhold Holtkamp, Sr., Werther Strasse 112, D4294 Isselburg, Fed. Rep. of Germany

[21] Appl. No.: 310,525

[22] Filed: Feb. 15, 1989

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Lucy characterized by its single, occasionally semi-double, dark lilac flowers with darker center; strong, upright flower stems that curve toward the center to form a compact bouquet above the leaves; medium green, oval to round leaves; profuse flowering, vigorous growth habit, flowering 10–11 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the culivar name Lucy.

The new cultivar was referred to during the breeding and selection process by the designation M 26, and is a product of a planned breeding program. The new cultivar was originated from a cross made by me in the controlled breeding program in Haffen, Federal Republic of Germany. The female, or seed parent was cultivar designated 4194. The male, or pollen parent was a cultivar designated 4196.

Lucy was discovered and selected by me as a flowering plant within the progeny of the stated cross in a controlled environment in Haffen, West Germany. Asexual reproduction of the new cultivar by leaf cuttings, as performed by me at Haffen, West Germany has demonstrated that the combination of characteristics as herein disclosed for the new cultivar are firmly fixed and retained through successive generations of asexual reproduction.

Lucy has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Lucy, which in combination distinguish this African violet as a new and distinct cultivar:

(1) Strong, upright flower stems curving toward the center.

(2) Dark lilac, single, occasionally semi-double flowers.

(3) Profuse flowering.

(4) Each plant carries 8–10 and more upright flower stems, each of which carries 7–10 and more flowers.

(5) Long lasting, non-dropping flowers.

(6) Vigorous grower.

(7) Plant saleable 10 to 11 weeks after potting.

(8) Seed capsules push slightly through.

(9) Medium green, oval to round leaves.

(10) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 1 p.m. in Nashville, Tenn.

Botanical Classification: *Saintpaulia ionantha,* Ramat., c.v. Lucy.

Parentage:

*Male parent.*—4196.

*Female parent.*—4194.

Propagation: The new cultivar holds its distinguishing characteristics through successive propagations by left cuttings.

Plant: From 9 cm to 11 cm tall when grown in pots, and approximately 25 cm to 28 cm in diameter when fully grown.

*Leaves.*—General form: Oval to round. Diameter: 65–75 mm. Texture: Leatherlike. Aspect: Shiny, hairy. Veins: Upperside: well visible. Underside: very well pronounced, light green, shiny. Color (upperside): Yellow-Green Group 147 A. Color (underside): Greyed-Green Group 194 C to D. Petiole: Very strong, reddish-brown hairy.

*Flowers.*—Buds: Ball-shaped, 6–8 mm just before opening, lilac. Sepals: Five (5). Color: Green with brownish touch. Calyx: Shape: Funnel-shaped. Aspect: Spear-shaped, hairy. Peduncle: Character: Strong upright, hairy. Color: Reddish-brown. Individual flowers: Size: 35–40 mm. Shape: Single violet-shaped (3 large and 2 small petals), occasionally semi-double. Color (upperside): Purple-Violet Group 80 A to B. Under cooler temperatures and more intensive lighting, the lilac color tends to intensify. Color (underside): Purple-Violet Group 80 B to C. Borne: Each flower stem carries 7–10 and more flowers on strong, upright peduncle that are free standing above the leaves, thereby forming a compact bouquet. Flowering Habit: Flowers 10–11 weeks after potting.

*Reproductive organs.*—Stamens: Two (2). Anthers: 2 composed of 4 anther cells, seed capsule pushes slightly through. Filaments: Yellowish green with purple traces, 4 mm long. Pollen Color: Yellow Group 7 A. Styles: 6 mm long, purple, base ovary light green and hairy.

*Roots.*—Normally developed, white when young, turning slightly brownish when older.

Disease resistance: Good.

General observations: Lucy has a very attractive appearance due to its dark lilac flowers contracting nicely with the bright yellow anthers. A tight bouquet of flowers free standing above the leaves develops after approximately 10–11 weeks. Each of the 8–10 and more flower stems carries 7–10 single, occasionally semi-double flowers. The color in the center of the flower is darker and radiates into the two small petals. The flowers are long-lasting and non-dropping and the seed capsules push slightly through. Medium green, oval to round leaves give the plant a fresh look.

I claim:

1. A new and distinct cultivar of African violet named Lucy, as described and illustrated, and particularly characterized by its single, occasionally semi-double, dark lilac flowers with darker center; strong, upright flower stems that curve toward the center to form a compact bouquet above the leaves; medium green, oval to round leaves; profuse flowering, vigorous growth habit, flowering 10–11 weeks after potting, and its long-lasting and non-dropping flowers.

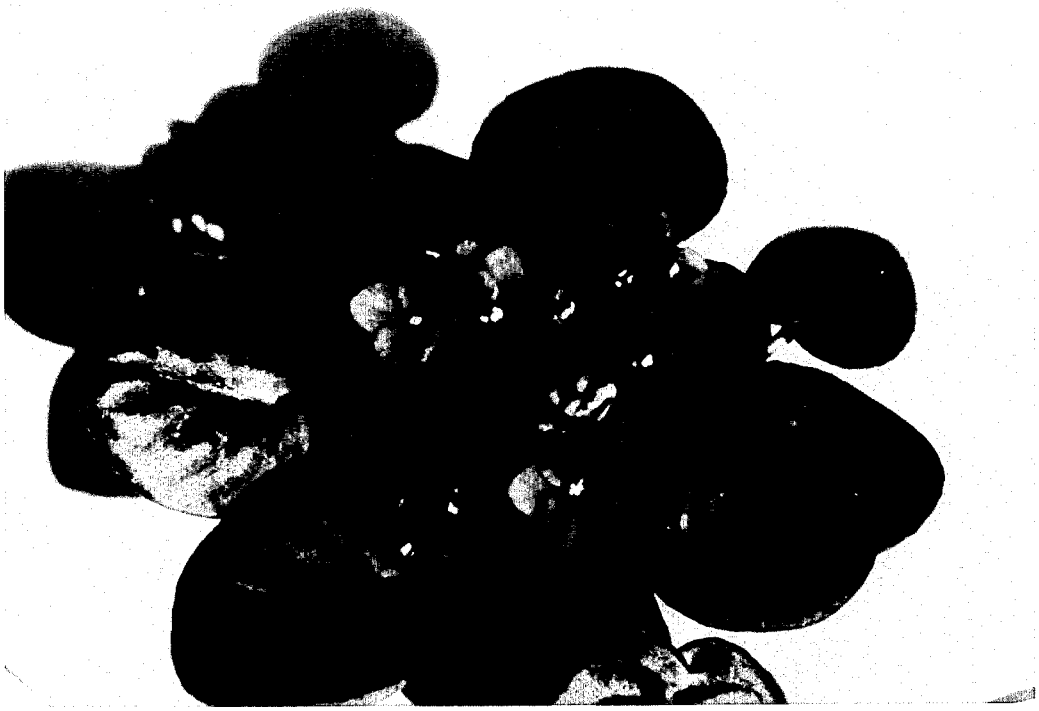

* * * * *